United States Patent
Utsunomiya

(10) Patent No.: US 7,195,738 B2
(45) Date of Patent: Mar. 27, 2007

(54) SENSOR AND DETECTING METHOD

(75) Inventor: Norihiko Utsunomiya, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/048,749

(22) Filed: Feb. 3, 2005

(65) Prior Publication Data
US 2005/0170405 A1    Aug. 4, 2005

(30) Foreign Application Priority Data
Feb. 3, 2004    (JP) .............. 2004-026813

(51) Int. Cl.
*G01N 27/00*    (2006.01)
*G01N 27/26*    (2006.01)
*G01N 27/30*    (2006.01)
*G01N 25/18*    (2006.01)
*G01N 25/48*    (2006.01)

(52) U.S. Cl. .................. 422/82.01; 422/50; 422/68.1; 422/82.02; 422/82.03; 436/149; 436/150; 436/806

(58) Field of Classification Search ............. 435/287.2, 435/288.3; 422/82.01
See application file for complete search history.

(56) References Cited

U.S. PATENT DOCUMENTS 5,286,362 A * 2/1994 Hoenes et al. ......... 204/403.04
5,399,256 A * 3/1995 Bohs et al. ................. 204/409
2003/0082601 A1 * 5/2003 Dill .............................. 435/6
2007/0004019 A1 1/2007 Hatakeyama et al. .... 435/173.6

OTHER PUBLICATIONS

Kojima et al., "Electrochemical protein chip with arrayed immunosensors with antibodies immobilized in a plasma-polymerized film", Mar. 1, 2003, Anal. Chem. vol. 75, pp. 1116-1122.*

* cited by examiner

*Primary Examiner*—Long V. Le
*Assistant Examiner*—Unsu Jung
(74) *Attorney, Agent, or Firm*—Fitzpatrick, Cella, Harper & Scinto

(57) ABSTRACT

A sensor is provided for detecting a target substance in a sample by detecting a product formed in the presence of an enzyme and an enzyme substrate. The sensor comprises two or more working electrodes, a first capturing molecule immobilized on the working electrodes, and a current-detector for detecting a current value flowing through at least one of the working electrodes. The sensor also comprises a target substance detection means having an arithmetic unit for determining an amount of the target substance in the sample on the basis of the current value detected by the current-detector in a specified period of time, and a crosstalk detecting electrode arranged between the working electrodes for detecting a crosstalk between the working electrodes. The specified period of time is a time necessary for the current value through the crosstalk detecting electrode to show a particular change.

3 Claims, 10 Drawing Sheets

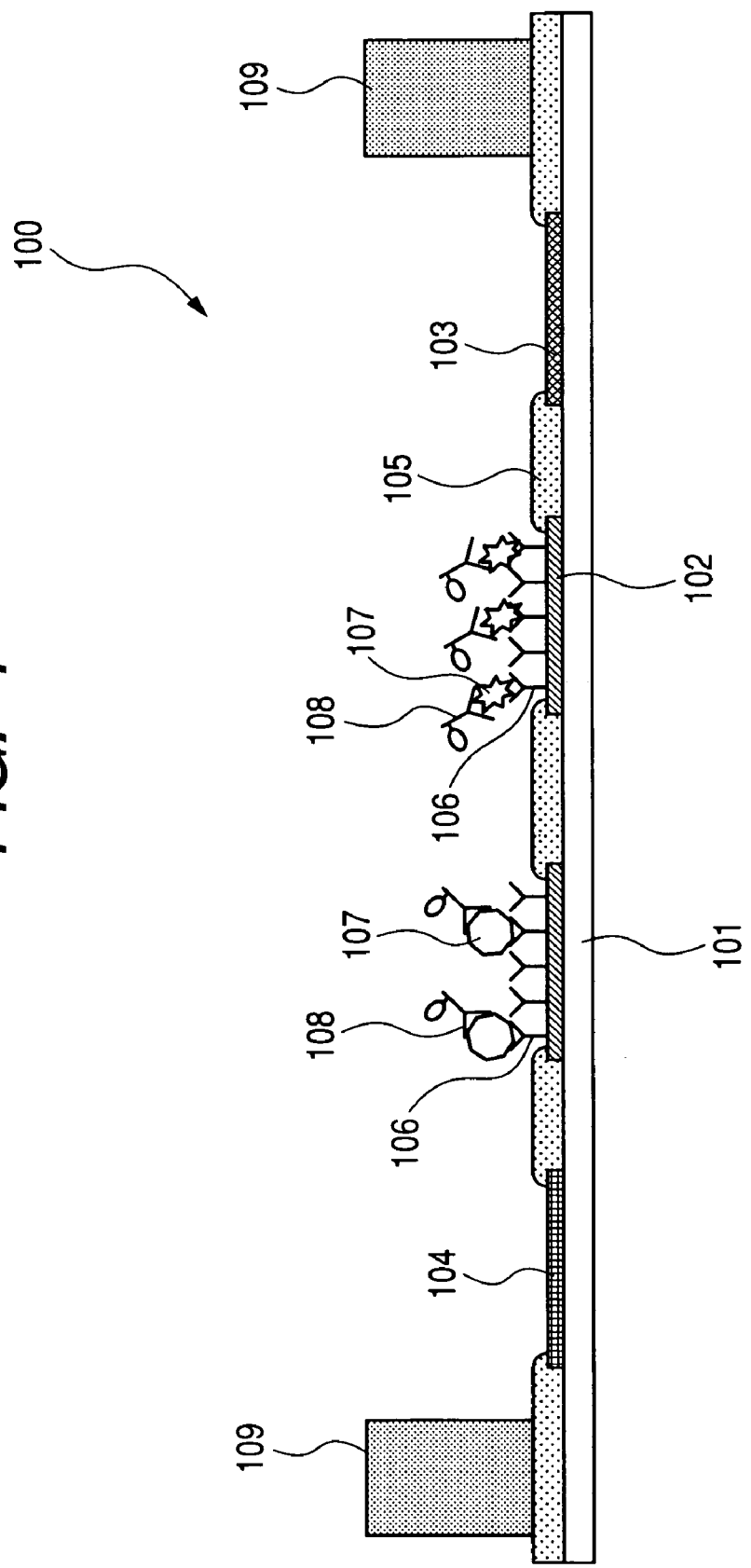

SENSOR AND DETECTING METHOD

BACKGROUND OF THE INVENTION

1. Field of the Invention

The present invention relates to a sensor and a detecting method; and particularly relates to the sensor for a sandwich immunoassay with the use of an enzyme-linked secondary antibody, which is an array-type sensor device for detecting a plurality of objective substances to be detected on the same device, and electrochemically detects a product formed by an enzyme reaction with an electrode, and to the detecting method.

2. Related Background Art

A detecting technique using an enzyme electrode method is known as a method for detecting a substance in a solution. The enzyme electrode method comprises immobilizing an enzyme on an electrode, making an enzyme substrate react with the immobilized enzyme, and measuring the amount of a reaction product by a current flowing through the electrode. The amount of the reaction product is proportional to the amount of the enzyme substrate, so that the amount of the enzyme substrate can be determined from the amount of the reaction product. Accordingly, in the detecting method, the objective substance to be detected is limited to the enzyme substrate.

A method for measuring other objective substances to be detected than an enzyme substrate includes a technology for detecting a plurality of antigens in a solution with electrodes placed on the same substrate, which is an array technology by an enzyme immunoassay, for instance. The array technology comprises immobilizing a kind of antibody on an electrode; reacting the immobilized antibody with a kind of antigen in a sample; reacting a secondary antibody with a captured antigen; and detecting a reaction product formed by the enzyme reaction of the secondary antibody with the electrode, to measure the concentration of the antigen. The array technology using the enzyme immunoassay is shown by Karube et al. in "Analytical Chemistry" 2003, 75, p. 1116–1122.

In order to detect various antigens on the same device by using an array sensor for an electrochemical immunoassay, it is necessary to narrow the space between working electrodes so as to increase the number of antigen species per unit area. On the other hand, an enzyme-reaction product diffuses which has been formed through an enzyme reaction by a secondary antibody coupled to the antigen captured by an immobilized antibody on a certain electrode. However, when the space between the working electrodes is narrow, a so-called crosstalk occurs which is a phenomenon of detecting the diffused enzyme-reaction product on an adjacent electrode.

SUMMARY OF THE INVENTION

The present invention is designed with respect to such a background art, provides a highly-integrated and miniaturized sensor capable of detecting a substance in a sample while preventing a detection error due to a crosstalk, and provides a detecting method thereof.

The present invention solves particularly the problem of the crosstalk, by previously determining a period of time involved in the diffusion, and determining the amount of an antigen only by a current value measured in the period.

According to an aspect of the present invention, there is provided a sensor for detecting a substance in a sample comprising:

composite-forming means which is comprised of a first capturing molecule and two or more electrodes, for forming on the two or more electrodes a composite comprising the first capturing molecule for specifically capturing the substance, the substance captured by the first capturing molecule and a second capturing molecule having a catalyst and being modified by the substance;

current-detecting means for detecting a current flowing through at least one of the working electrodes having the catalyst thereon so as to detect a product formed when a catalytic substrate capable of acting with the catalyst is contacted with the catalyst; and substance-detecting means for determining the amount of the substance in the sample on the basis of the current value detected by the current-detecting means in a specified period of time after the catalyst has contacted with the catalytic substrate.

The substance-detecting means preferably determines the amount of the product from the current value, and then determines the amount of the substance in the sample from the amount of the product. The specified period of time is preferably shorter than the time necessary for the product to reach at least one of the electrodes adjacent to the electrode having the catalyst thereon which has formed the product. The sensor preferably further comprises an electrode for detecting a crosstalk between the electrodes, wherein the specified period of time is the time necessary for the current flowing through an electrode for detecting the crosstalk to show a particular change; and means for determining the captured amount of the substance, on the basis of the value of the detected current flowing through the electrode having the catalyst, in the period of time before the current has shown the particular change.

Alternatively, the first capturing molecule preferably has a different specie on each of two or more electrodes from that of other bodies.

According to another aspect of the present invention, there is provided a detecting method for detecting a substance in a sample comprising the steps of:

forming on two or more electrodes a composite comprising a first capturing molecule for specifically capturing the substance, the substance captured by the first capturing molecule and a secondary-capturing molecule having a catalyst and being modified by the substance; detecting a current flowing through a working electrode having the catalyst thereon so as to detect a product formed when a catalytic substrate capable of acting with the catalyst contacts with the catalyst; and determining the amount of the substance in the sample on the basis of the value of the current detected in a specified period of time after the catalyst has contacted with the catalytic substrate.

The step of determining the amount of the substance in the sample preferably comprises determining the amount of the product from the value of the current, and determining the amount of the substance in the sample from the amount of the product.

A method for determining the amount of the substance in the sample (hereinafter also referred to as "target substance"), on the basis of the value of current detected by the current-detecting means in a particular period after the catalytic substrate has contacted with the sensor, in the substance-detecting means and the step for determining the amount of target substance in the sample, includes a method for determining the amount of a product from the above current value and determining the amount of the substance in the sample from the amount of the product.

A sensor according to the present invention forms a composite of "first capturing molecule—target substance—second capturing molecule modified by a catalyst (hereafter called "a catalyst-linkedlinked second capturing molecule")", on a working electrode. The target substrate can be introduced in the state. A period of time necessary for a resulting product from the catalytic reaction to reach an adjacent working electrode through the diffusion may be previously determined by a technique like an experimental trial. Then, a captured amount of the target substance can be determined on the basis of a current value measured in the period after a substance to be reacted on a catalyst as the catalytic substrate (hereafter called a "catalyst substrate" or simply "a substrate") has been introduced.

A first capturing molecule and a catalyst-linked second capturing molecule are hereinafter referred to as a "primary capturing molecule" and a "secondary capturing molecule", respectively.

In the present invention, a user can previously set the period arbitrarily.

In the present invention, each working electrode can have each different combination of a primary capturing molecule and a target substance. Specifically, in the present invention, the combinations of a plurality of primary capturing molecules and target substances can be simultaneously employed.

In addition, in the present invention, a sensor having a plurality of working electrodes arranged thereon at even spaces can be comprised of a working electrode for detecting a crosstalk between adjacent working electrodes which are specialized for detecting a crosstalk current due to diffusion of the reaction product from at least one adjacent site. The sensor can arrange at least one working electrode adjacent to the working electrode for detecting the crosstalk on which the same catalyst as the catalyst for modifying the second capturing molecule is previously immobilized.

In the present invention, the sensor detects only a current flowing before the time when a crosstalk due to diffusion occurs, to prevent the degree of detection accuracy from degrading due to the crosstalk. Furthermore, the sensor can narrow the space between working electrodes, so that it can reduce the size of the sensor or mount a lot of working electrodes on the sensor having the same size.

BRIEF DESCRIPTION OF THE DRAWINGS

FIG. 1 is a schematic sectional view of a sensor element, showing a sensor according to the embodiment 1 in the present invention;

DESCRIPTION OF THE PREFERRED EMBODIMENTS

Figure 2A:
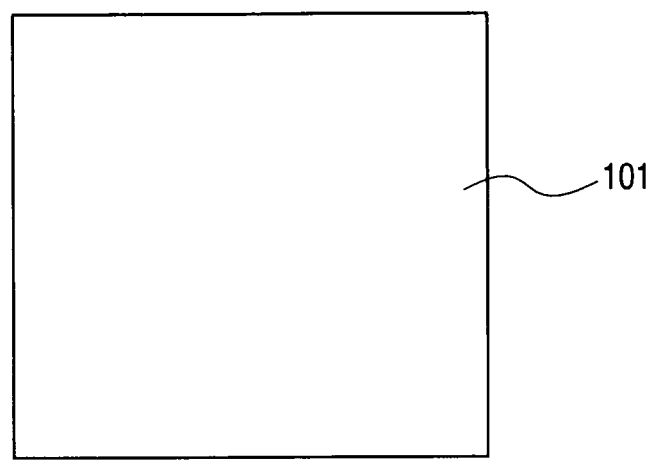
FIGS. 2A, 2B and 2C are process drawings showing steps in the first half of a process for producing a sensor according to the embodiment 1 in the present invention.

The present invention will be described in detail below.

A sensor according to the present invention is a sensor for detecting a target substance in a sample, comprising: means for making three substances of (1) a primary capturing molecule for capturing the target substance, which is immobilized on at least two working electrodes placed at different positions, (2) the primary capturing molecule, the target substance and a second capturing molecule modified by a catalyst, form a composite having a configuration of "primary capturing molecule—target substance—catalyst-linked secondary capturing molecule";

(3) means for introducing a substrate corresponding to the catalyst to a region in which the composite exists, and forming a product by the action of the catalyst;

(4) means for contacting the product of catalystic reaction with the working electrode, and detecting the product by a current flowing through the working electrode; and (5) means for determining the captured amount of the target substance, on the basis of the value of a current flowing in a previously determined certain period of time after the substrate has been introduced.

In addition, a sensor according to the present invention is a sensor for detecting a target substance in a sample, comprising: means for making three substances of (1) a primary capturing molecule for capturing the target substance, which is immobilized on at least two working electrodes placed at different positions, (2) the primary capturing molecule, the target substance and a second capturing molecule linked with a catalyst, form a composite having a configuration of "primary capturing molecule—target substance—catalyst-linked secondary capturing molecule";

(3) means for introducing a substrate corresponding to the catalyst to a region in which the composite exists, and forming a product by the action of the catalyst;

(4) means for contacting the product formed by the catalyst with the working electrode, and detecting the product by the current flowing through the working electrode, wherein (5) the working electrodes are placed at different positions on a line or a plane at regular spaces; and further comprising:

(6) at least one working electrode for detecting a crosstalk between adjacent working electrodes;

(7) means for monitoring the value of a current flowing through the working electrode for detecting a crosstalk, after the time when the catalyst substrate has been introduced; and (8) means for determining the captured amount of the target substance on the basis of the value of a current flowing through the electrode for detecting the crosstalk, during the period after the catalyst substrate has been introduced and before the current value shows the predetermined change.

A sensor according to the present invention can arrange a working electrode on which a catalyst corresponding to the substrate is previously immobilized, adjacent to the working electrode for detecting a crosstalk.

A detecting method according to the present invention uses a sensor employing a primary capturing molecule for capturing the target substance, which is immobilized on at least two working electrodes placed at different positions, comprising the steps of:

(1) making three substances of the primary capturing molecule, the target substance and a secondary capturing molecule linked with a catalyst, form a composite having a configuration of "primary capturing molecule—target substance—catalyst-linked second capturing molecule";

(2) introducing a substrate corresponding to the catalyst to a region in which the composite exists, and forming a product by the action of the catalyst;

(3) contacting the product formed by the catalyst with the working electrode, and detecting the product from a current flowing through the working electrode; and (4) determining the captured amount of the target substance, on the basis of the value of a current flowing in a previously determined certain period of time after the substrate has been introduced.

A detecting method according to the present invention with the use of the sensor which places the working electrodes at different positions on a line or a plane at regular spaces, and arranges at least one electrode for detecting a crosstalk between adjacent working electrodes, further comprises the steps of:

(1) monitoring the value of a current flowing through the working electrode for detecting a crosstalk, after the time when the catalyst substrate has been introduced; and (2) determining the captured amount of the target substance on the basis of the value of a current flowing through the electrode for detecting a crosstalk, during the period after the catalyst substrate has been introduced and before the value of the current shows a predetermined change.

One example of a sensor element constituting a sensor according to the present invention is shown in a sectional view of FIG. 1. Reference character 100 denotes the sensor element. A sensor substrate 101 is made of a material which can be easily patterned with a lithography process, and is not particularly limited so long as having no electroconductivity at least on the surface. Glass or a silicon wafer having an insulation film on the surface is generally used as a material of the sensor substrate. A working electrode 102 is preferably made of a material on the surface of which a primary capturing molecule can be easily immobilized, and the surface of which is hardly deteriorated by oxidation or the like. Gold is employed in an embodiment shown below as the material of the primary capturing molecule. A reference electrode 103 is preferably a silver/silver halide electrode. In the present embodiment, a silver/silver chloride (Ag—AgCl) electrode is used. An auxiliary electrode 104 is used only for forming the reference electrode 103, so that the material is not limited so long as the surface is hardly deteriorated by oxidation, reduction and the like. In the present embodiment, a platinum electrode is used therefor.

An insulative protection layer 105 is preferably formed of a photosensitive polyimide as the material, because it is easily patterned. An immobilized primary capturing molecule 106 is preferably a protein, a nucleic acid, a sugar chain, a lipid, a part thereof or a composite thereof. In the present embodiment, an antibody of a protein is used.

A target material 107 is preferably a protein, a nucleic acid, a sugar chain, a lipid, a part thereof or a composite thereof; and may be an antigen as shown in the present embodiments described below. A substance capable of discriminating an antibody, or equivalently, having antigenicity, can be a preferable target substance. An example for the combination of a target substance and a primary capturing molecule includes DNA-DNA (hybridization), ligand-receptor protein or sugar chain-lectin protein.

A secondary capturing molecule 108 is defined as a substance consisting of a catalyst and a substance capable of discriminating and capturing the target substance and combining the catalyst, i.e. a second capturing molecule. The second capturing molecule may be the same as or similar to the primary capturing molecule 106. An enzyme, a biocatalyst, is preferable as the catalyst in the present invention. In the present embodiment described below, an antibody is used as the second capturing molecule, and an enzyme is used as a catalyst of the secondary capturing molecule. As the enzyme, glucose oxidase is employed in the Examples so as to allow a general catalyst substrate being used. Although not shown in FIG. 1, such a glucose is provided in a form of a glucose solution in the embodiment of the figures.

As for the combination of enzyme with substrate, any combination can be used so long as a product formed by the enzyme as the catalyst causes a detectable change of a current value, when it contacts with a working electrode. The other example of the combination of enzyme with substrate than the example of glucose oxidase includes that of alkaline phosphatase-phosphoric ester, malate oxidase-malic acid, glutamate oxidase-glutamic acid, uricase-uric acid, lactate oxidase-lactic acid and glycerol oxidase-glycerine. The material of a cell wall 109 for forming the reaction cell of a sensor is not limited so long as it can be firmly bonded to an insulative protection layer 105.

Figure 4:
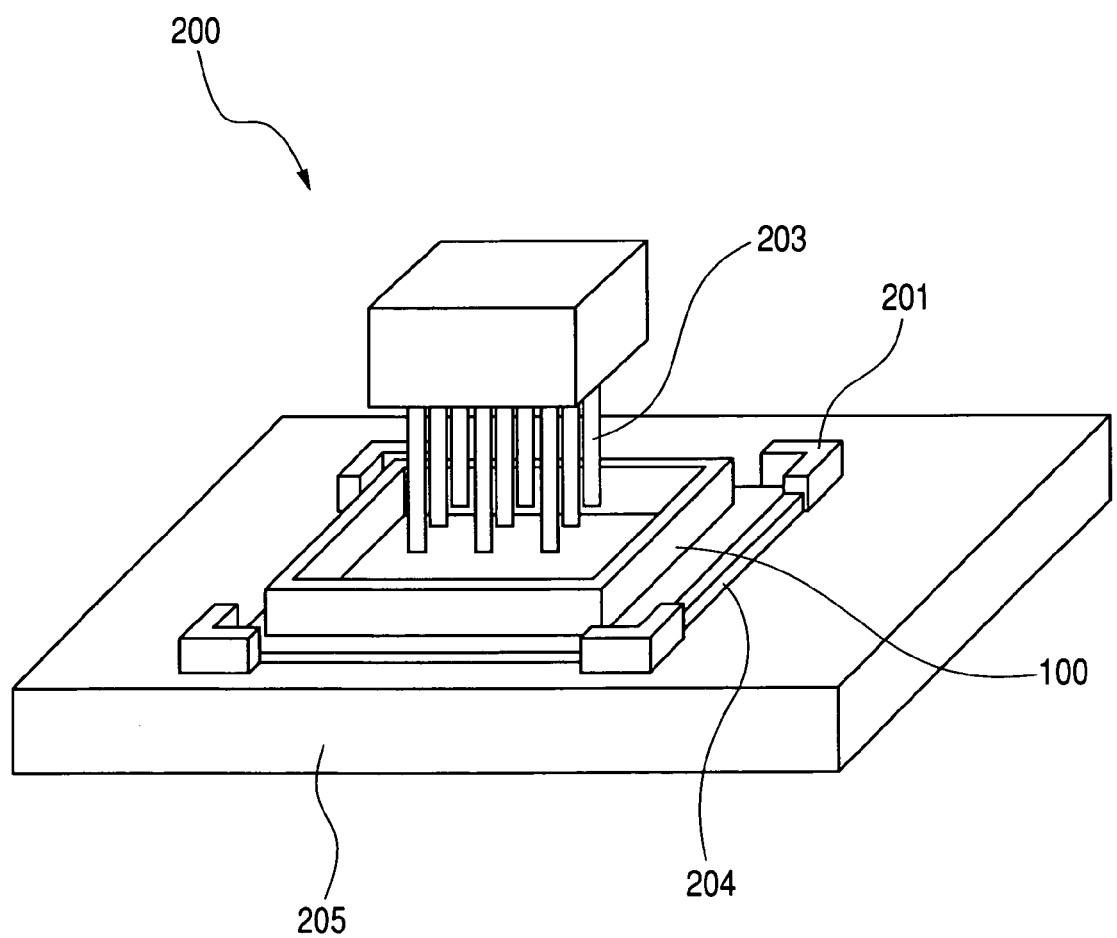
FIG. 4 is a schematic view showing the outline of a measuring module consisting of a sensor element and the main body of measuring module according to the embodiment 1 in the present invention.
Figure 5:
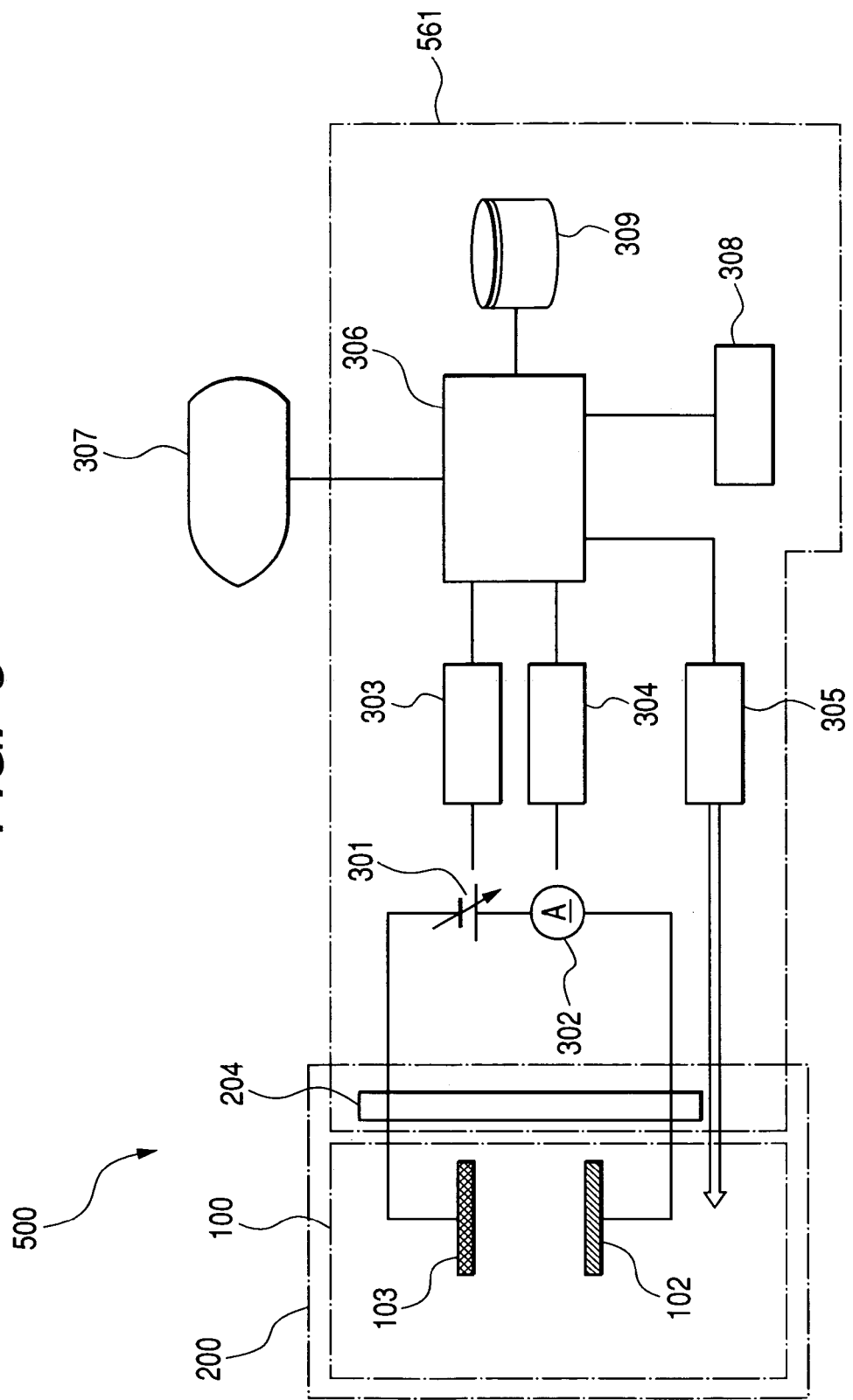
FIG. 5 is a block diagram of a sensor element and the main body of a measuring apparatus according to the embodiment 1 in the present invention.

The function of sequence control for sampling, which is a characteristic of a sensor according to the present invention, relies on the main body of a measuring apparatus which is a part of the measuring apparatus except the sensor element. This will be described in FIGS. 4 and 5. FIG. 4 shows the outline of a measuring module which consists of a main body of measuring module in the main body of measuring apparatus and a sensor element comprised of a sensor according to the present invention. The main body of measuring module comprises a base 205 for the main body of measuring module, a sensor holder 201 for fixing the sensor element 100, a sample reagent-supplying nozzle 203 and a sensor electrode connector 204. Both of sensor holder 201 and base 205 are required to fix solely the sensor element, so that the materials thereof are not limited. The sample reagent-supplying nozzle 203 is solely required to accurately control a fluid volume and to be made of a material having resistance to a sample reagent, and therefore the material is not limited. The sensor electrode connector 204 electrically connects the sensor element to the main body of measuring apparatus. The connector has only to have a function of electrically connecting them, and the material is not limited as far as such a function is fulfilled. FIG. 5 shows a functional block diagram of a measuring apparatus 500 comprising the main body of measuring apparatus and the sensor element according to the present invention.

With reference to FIGS. 4 and 5, the outline of a measuring apparatus 500 according to the present invention will be now described. The measuring apparatus 500 comprises a sensor element 100 a sensor according to the present invention, and a main body 561 of the measuring apparatus.

The main body 561 of measuring apparatus comprises the main body of measuring module and other parts which are not included in the measuring module. A region to be included in the measuring module of the main body of measuring apparatus may be appropriately designed. For example, the base for the main body of measuring module as denoted by numeral 205 in FIG. 4 may be integrated with a base of the main body of measuring apparatus. The outline of the main body of measuring apparatus will be now described below. A sequence control necessary for the present invention is controlled by an arithmetic unit 306. After the arithmetic unit 306 has directed a nozzle controller 305 to feed a catalyst substrate, an A/D converter 304 is controlled so as to acquire a current value only in an assigned period of time. Due to the above configuration, the sensor can detect the current value only before a crosstalk resulting from diffusion occurs, and can prevent the degree of detection accuracy from degrading due to the crosstalk. Furthermore, the sensor can narrow the space between working electrodes, and consequently reduce the size of the sensor or place many working electrodes if the sensor has the same size. In addition, a user can previously and arbitrarily set the period of time before the crosstalk occurs, so that the sensor can cope with the crosstalk time which varies according to conditions when the sensor is used. Thus, the sensor can singly detect a plurality of target substances; can detect different target substances at each area therein; and can reliably prevent the degree of accuracy from degrading due to the crosstalk, because the necessary time for a catalyst product to diffuse to other working electrodes can be actually measured on the sensor, and because the crosstalk time can be reliably measured, even when no objective target substance or the very little amount of it exists in a sample.

A detailed embodiment will be now described with reference to embodiments below.

INDUSTRIAL APPLICABILITY

A sensor according to the present invention is a highly-integrated and miniaturized sensor which can detect substances in a sample while preventing a detection error due to a cross talk, so that it can be used in apparatuss for a clinical examination required to simultaneously detect many items.

EMBODIMENTS

A sensor according to the present invention will be now described with reference to following embodiments. The present invention is not limited by the descriptions of the following embodiments.

Embodiment 1

The configuration of a sensor element according to the present embodiment is shown in FIG. 1 as a sensor element 100. A substrate 101 has a working electrode 102 and a reference electrode 103 on a substrate surface. The substrate surface except the working electrode and the reference electrode is covered by an insulative protection layer (an insulation film) 105. On the working electrode 102, an immobilized antibody (hereafter called "a primary antibody" as well) 106 is immobilized as the primary capturing molecule. In the present embodiment, the type of an antibody 106 is selected so as to make each working electrode capture a different type of an antigen 107, and is immobilized on each working electrode.

For a secondary capturing molecule 108, an enzyme-linked antibody (hereafter called "a secondary antibody" as well) is adopted. The antibody 108 is coupled to an antigen, so as to sandwich the antigen to be captured cooperatively with the immobilized antibody 106, when the sensor is used. Accordingly, a composite comprises an immobilized antibody 106 as the primary capturing molecule, the antigen 107 and an enzyme-linked antibody 108 (though the antigen 107 and the antibody 108 are not the components of a sensor element 100). The primary antibody to be immobilized and the secondary antibody 108 are provided as reagents used together with the sensor. A cell wall 109 composes the reaction cell of a sensor chip, and working electrodes 102 and reference electrodes 103 are configured in the reaction cell surrounded by the cell wall.

<Method for Producing Sensor Element>

With reference to FIGS. 2A to 2C and 3A to 3C, a process of producing a sensor element according to the present invention will be described now.

As shown in FIG. 2A, a glass base 101 is prepared which is the base substrate of a sensor element according to the present invention.

Figure 2B:
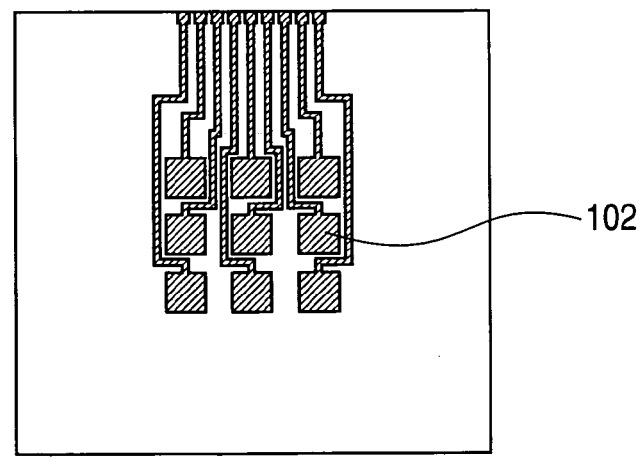

As shown in FIG. 2B, working electrodes 102 of gold (Au), lead wires and contact points 111 of a sensor are patterned on the same base with the use of a liftoff process.

Figure 2C:
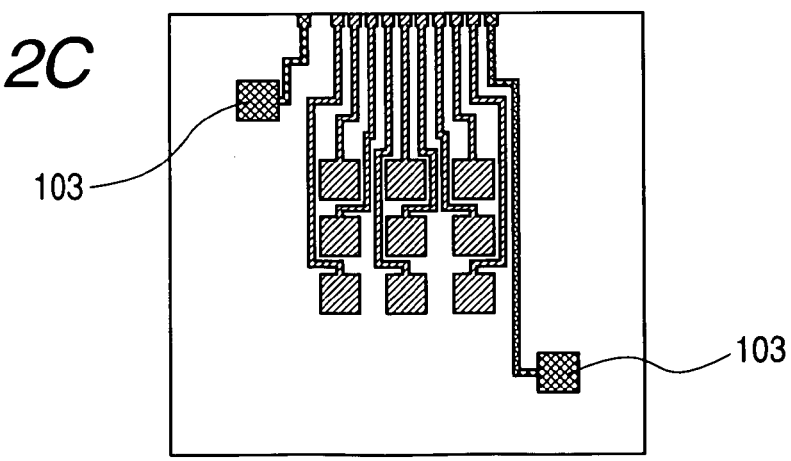

Subsequently, reference electrodes 103 are formed on a gold (Au) thin film, and a silver (Ag) thin film is formed as shown in FIG. 2C.

Figure 3A:
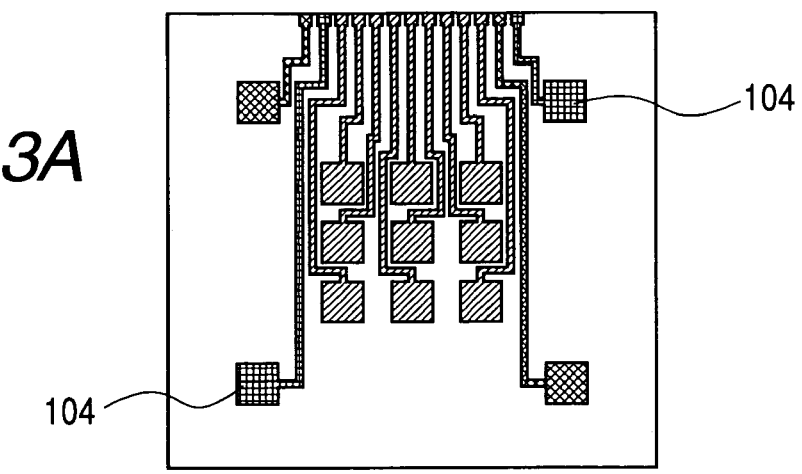
FIGS. 3A, 3B and 3C are process drawings showing steps in the latter half of a process for producing a sensor according to the embodiment 1 in the present invention.

Furthermore, auxiliary electrodes 104 which are used when a reference electrode are formed, are formed as shown in FIG. 3A. The auxiliary electrodes are made by patterning platinum (Pt) on a substrate.

Figure 3B:
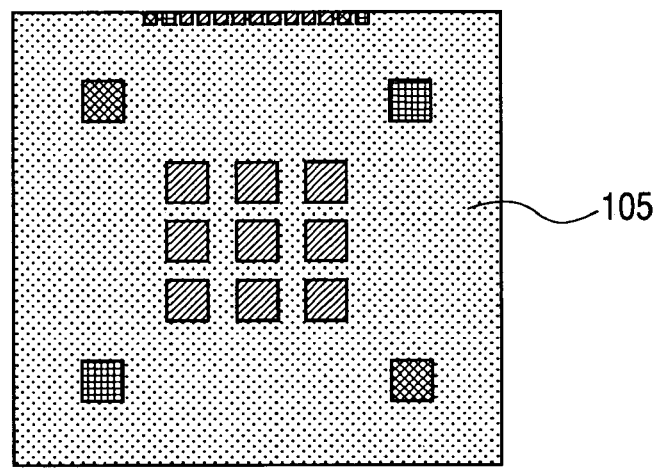

Each of reference electrodes 103 and auxiliary electrodes 104 are formed with the use of a liftoff process as well. As shown in FIG. 3B, in order to expose only a sensor electrode part, and insulation-protect the base and an electrode lead wire portion except the above part, an insulative protection film 105 is formed on the base. The insulative protection film can be formed with the use of a photosensitive polyimide resin.

Figure 3C:
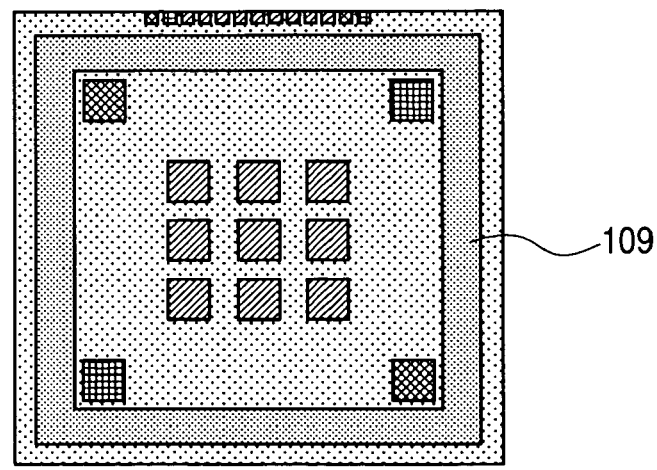

Then, as shown in FIG. 3C, a cell wall 109 for forming a reaction cell is formed into the shape of surrounding a sensor periphery. The cell wall is made of an epoxy resin, and is bonded to the base with an adhesive having a water proofing property. Furthermore, a silver/silver chloride (Ag—AgCl) electrode is formed on reference electrodes 103 made of silver (Ag). The silver/silver chloride electrode is formed by the steps of pouring a KCl—HCl solution into the reaction cell of a chip, and applying a constant current between the auxiliary electrode and the reference electrode. Subsequently, an antibody to be immobilized is immobilized on working electrode 102. Before immobilization, the surface of the working electrodes made of gold (Au) are treated with thiol having an NHS group. After the thiol treatment, each solution containing a different antibody to be immobilized is added onto each working electrode dropwise. A sensor element is obtained with the above steps.

<Configuration of Measuring Apparatus>

Subsequently, the configuration of a measuring apparatus for measuring the amount of an antigen in a real sample with the use of the sensor element 100 will be described with reference to FIGS. 4 and 5. The sensor element 100 is electrically connected to the substrate 205 of the main body of a measuring module 200 through a sensor electrode connector 204. The connector has contact points corresponding to each of working electrodes 102, auxiliary electrodes 104 and reference electrodes 103, and passes on detected electric signals for characteristics and applied voltage, from/to the main body 561 of measuring apparatus. Above a sensor holder, a nozzle 203 is installed so as to add an enzyme substrate dropwise onto a sensor. The nozzle 203 is formed of each nozzle communicating with each working electrode, and each nozzle is placed so as to be vertical on the center of each working electrode.

FIG. 5 is a functional block diagram of a measuring apparatus 500 constituted by a sensor element 100 according to the present embodiment and the main body 561 of measuring apparatus, which are connected with each other. Each electrode in the sensor element 100 is electrically connected with the main body of measuring apparatus through a sensor electrode connector 204, as described above.

An electric potential can be applied between a reference electrode 103 and a working electrode 102 by a power source 301. A D/A converter 303 receives a directed value of voltage from an arithmetic unit 306, and controls the power source so as to control the voltage value. The current flowing between the electrodes is detected by a current-detecting section 302. The current value outputted from a current-detecting section 302 is taken in the arithmetic unit 306 through an A/D converter 304.

A nozzle controller 305 makes a nozzle 203 add an enzyme substrate solution of a specified value dropwise, on the basis of a direction from the arithmetic unit 306. In order to display measured results, a display 307 is arranged. So as to input parameters to be used in the measurement described below, an input device 308 of a keyboard is arranged. A fixed disk 309 is installed so as to save the parameters.

<Reaction Process>

An actual process for measuring an antigen while using a sensor element and a measuring apparatus will be now described. A mixed solution is prepared which contains a plurality of secondary antibodies corresponding to the type of an antigen to be detected in each working electrode. An example of a modifying enzyme includes glucose oxidase. A sample solution containing the antigens is mixed with the solution of the secondary antibody to react each other. The mixed solution of the sample and the enzyme-linked second antibody after having finished the reaction is poured into the reaction cell of a sensor element, to react the composite of the secondary antibody and the antigen in the mixed solution, with a primary antibody previously immobilized on the working electrode. After the reaction, the reaction cell is cleaned, a phosphoric acid buffer solution is poured into the reaction cell, and the sensor element is fixed in the main body of measuring module in the main body of measuring apparatus. Further, although the display 307 is not incorporated in the main body 501, the display maybe incorporated therein. For instance, when the display is comprised in a computer comprised of the arithmetic unit 306, the input device 308, the fixed disc 309 and so forth which are also incorporated in the main body 501, the display may be incorporated in the main body 501.

In the present embodiment, the reaction of a secondary antibody with an antigen was carried out at first, but the antigen may be reacted with an immobilized antibody at first, and then reacted with the secondary antibody.

<Operation Algorithm>

After a fixing operation for the sensor element has been finished, the amount of an antigen captured by an immobilized antibody is measured with the use of the main body of a measuring apparatus. The procedure will be described with reference to the flow chart shown in FIG. 6.

Figure 6:
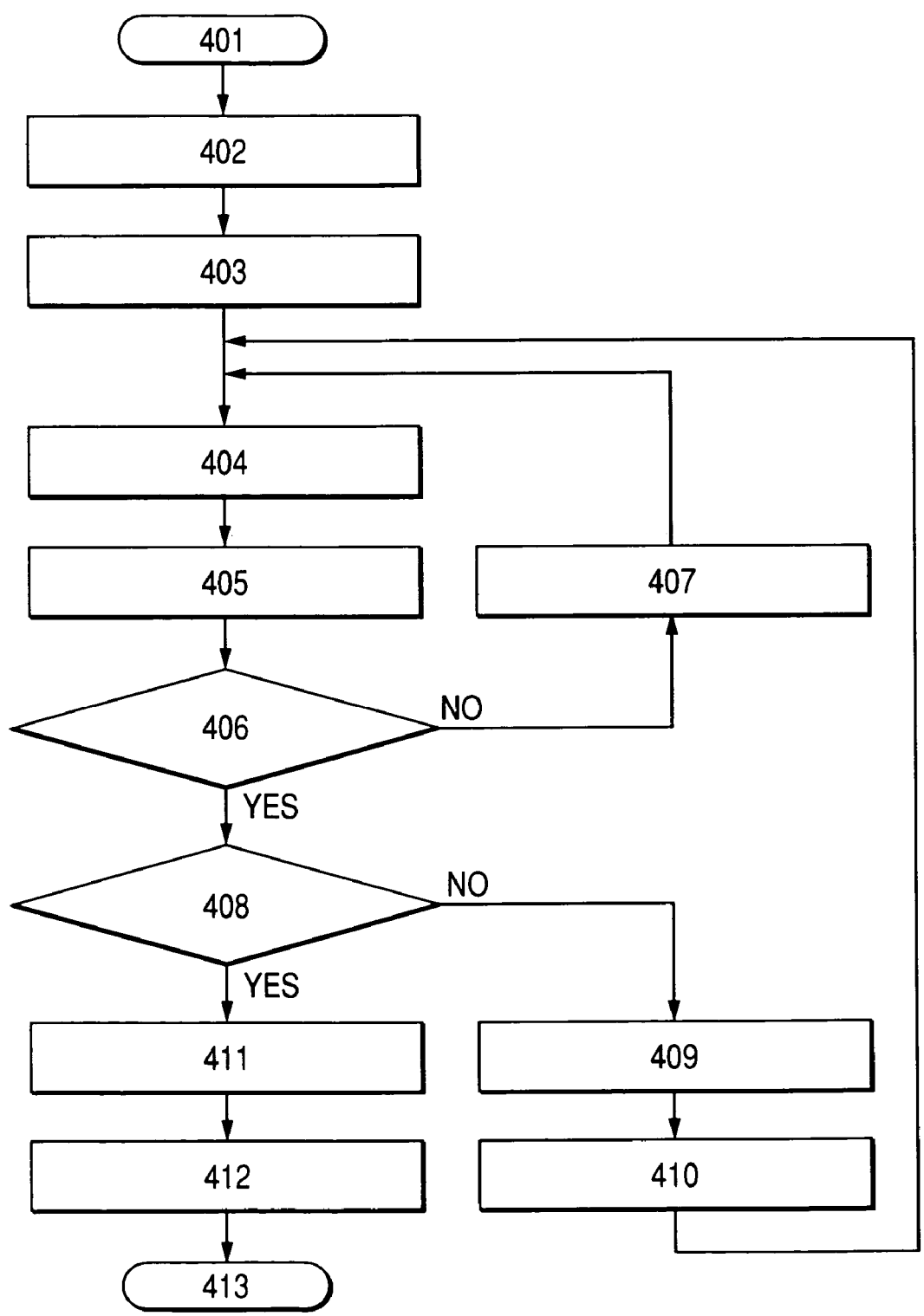
FIG. 6 is a flow chart showing an operation process for a sensor signal according to the embodiment 1 in the present invention.

By inputting a command for starting an operation from an input device 308 such as a keyboard shown in FIG. 5, the operation in FIG. 6 is started (the step 401).

Predetermined voltage is applied to each working electrode according to directions from a CPU (the step 402).

According to the directions of CPU, a predetermined amount of an enzyme substrate solution is added onto each working electrode through a nozzle above it (the step 403). The enzyme substrate to be used here needs to be an enzyme substrate corresponding to an enzyme by which the second antibody was modified. When glucose oxidase is used as an enzyme, a glucose solution needs to be used as the enzyme substrate. Then, the current detected in the electrode in the next step is supposed to detect the amount of hydrogen peroxide produced by an enzyme reaction.

In the operation steps 404 to 407, the apparatus detects a current outputted from each working electrode for the all electrodes.

The apparatus detects a current in the step 404; saves the value of the detected current in a fixed disk in the step 405; and in the step 406, judges whether the all working electrodes are examined, or not. If it has been judged that the all electrodes are not examined, the channel is changed to a next working electrode in the step 407.

When it has been judged in the step 406 that data have been acquired from all working electrodes, it is judged in the step 408 whether a predetermined limited period of time for measurement has elapsed after the measurement has started, or not. For the predetermined limited period of time for measurement, a fixed value or a set value saved on the fixed disk, which has been previously input from a keyboard, may be used.

When the apparatus has judged in the step 408 that a predetermined limited period of time for measurement has not yet elapsed, the apparatus waits for a period of a sampling interval in the step 409. For the sampling interval, a fixed value or a set value saved on the fixed disk, which has been previously input from a keyboard, may be used. Subsequently in the step 410, the apparatus switches a channel to the first working electrode, and carries out steps starting from the step 404 for measuring the value of a current flowing through each working electrode.

When the apparatus has judged in the step 408 that a predetermined limited period of time for measurement has elapsed, it statistically analyzes current values sampled on each working electrode, in the step 411, displays the concentration of an antigen corresponding to each working electrode on a display on the basis of the statistically analyzed values, in the step 412, and finishes the operation in the step 413. The statistically analyzed values obtained from the statistical analysis in the step 411 are values represented by an average value, an integral value and a maximum value within the predetermined limited period of time for measurement.

Embodiment 2

Figure 7:
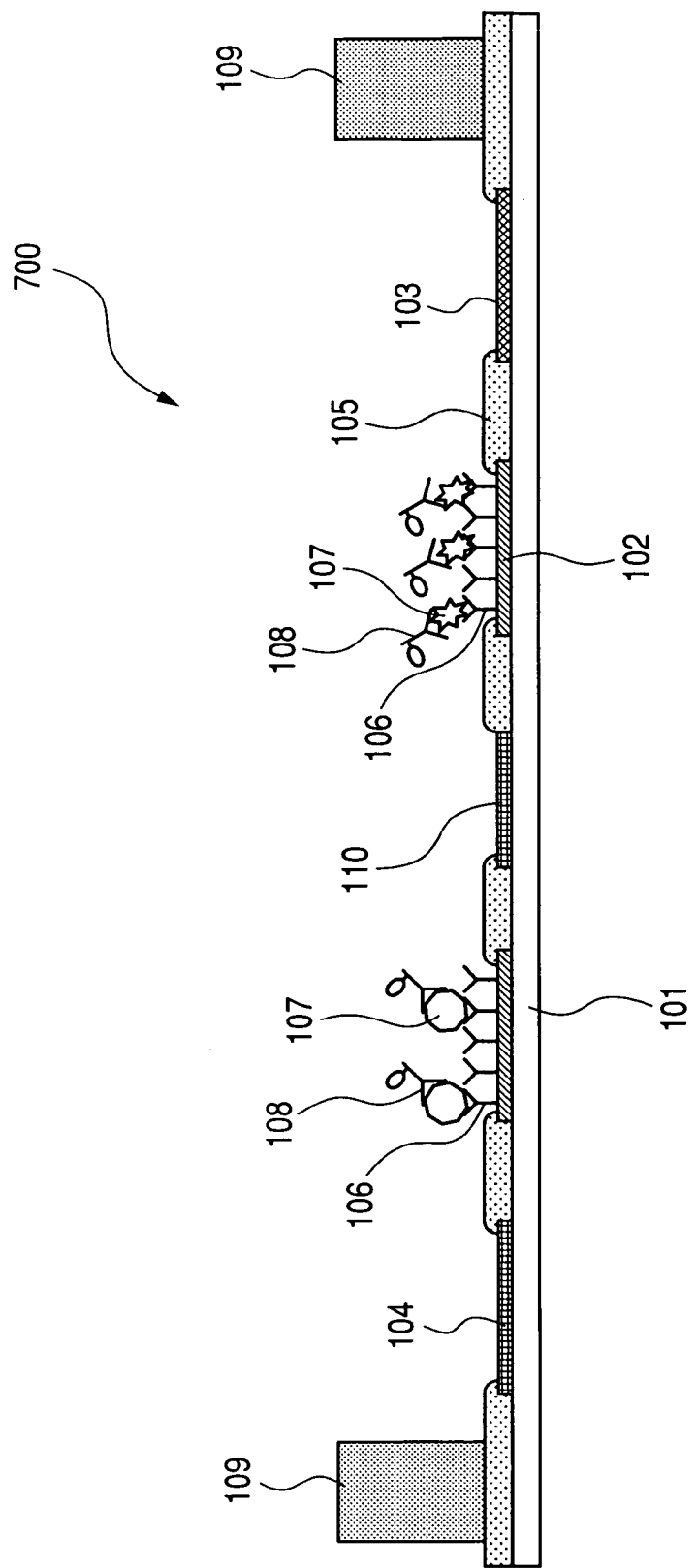
FIG. 7 is a sectional view of a sensor element, showing a sensor according to the embodiment 2 in the present invention.

A sectional view for the configuration of a sensor element 700 according to the present embodiment is shown in FIG. 7. The sensor element 700 has the same configurations for 101 to 109 as those in the sensor element 100 according to the embodiment 1, but is different from the sensor element 100 in the point of having working electrode for detecting a crosstalks added as shown by 110 in FIG. 7.

Figure 8:
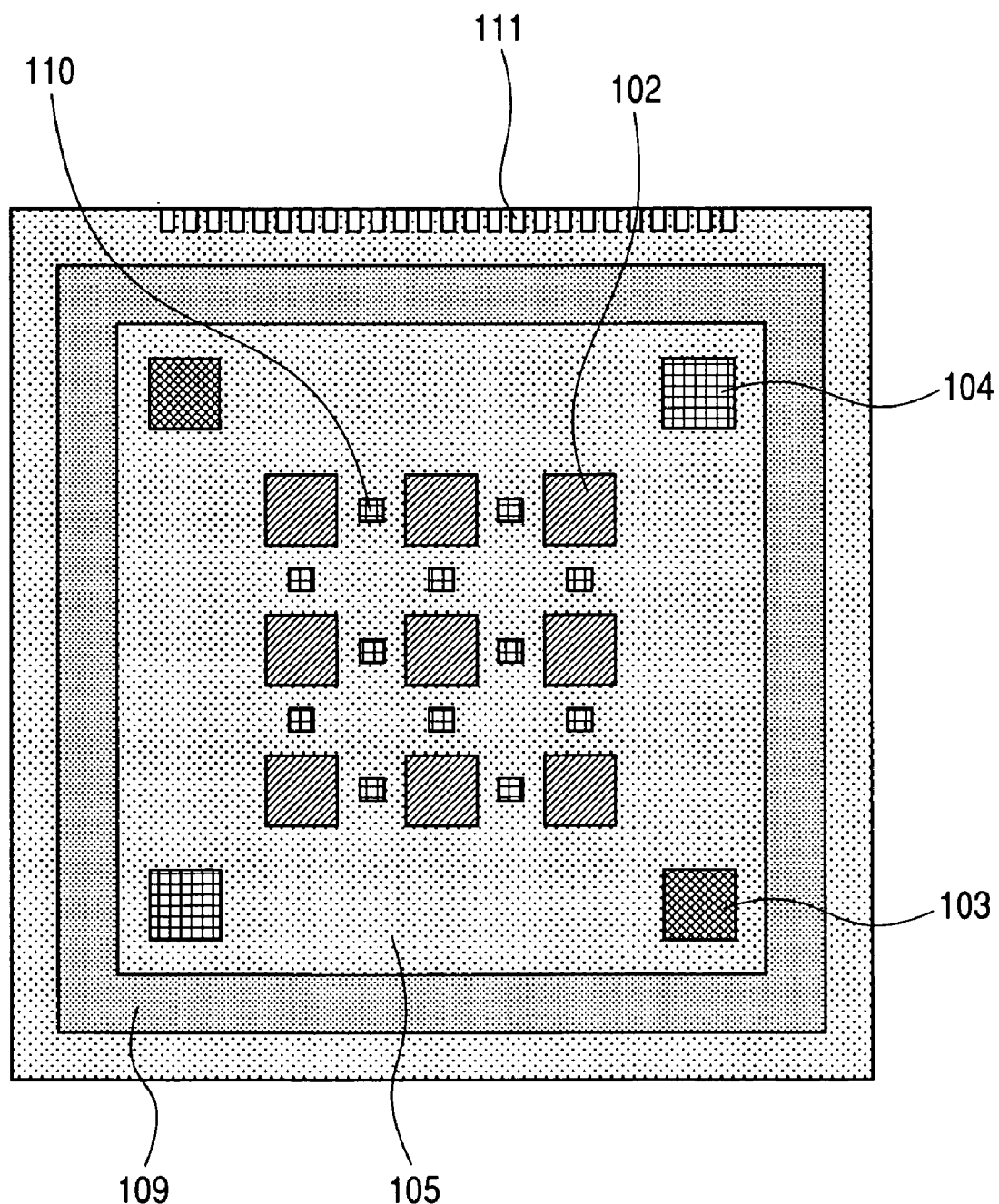
FIG. 8 is a plan view of a sensor element, showing a sensor according to the embodiment 2 in the present invention.

The working electrode 110 for detecting a crosstalk is arranged between the working electrodes 102, as shown in FIG. 8. A method for producing a sensor element according to the present embodiment is approximately same as a method for producing the sensor element according to the embodiment 1 shown in FIGS. 2A to 3C; but is different from that of the embodiment 1 in forming working electrodes 110 for detecting the crosstalk with a liftoff process, when forming the working electrode 102 in the step shown in FIG. 2B. It is natural as shown in FIG. 7 that an antibody is not immobilized on the working electrode 110 for detecting the crosstalk. A measuring apparatus for detecting an antigen with the use of a sensor element 700 according to the present embodiment has the same configuration as that of FIGS. 4 and 5 shown in the embodiment 1.

Figure 9:
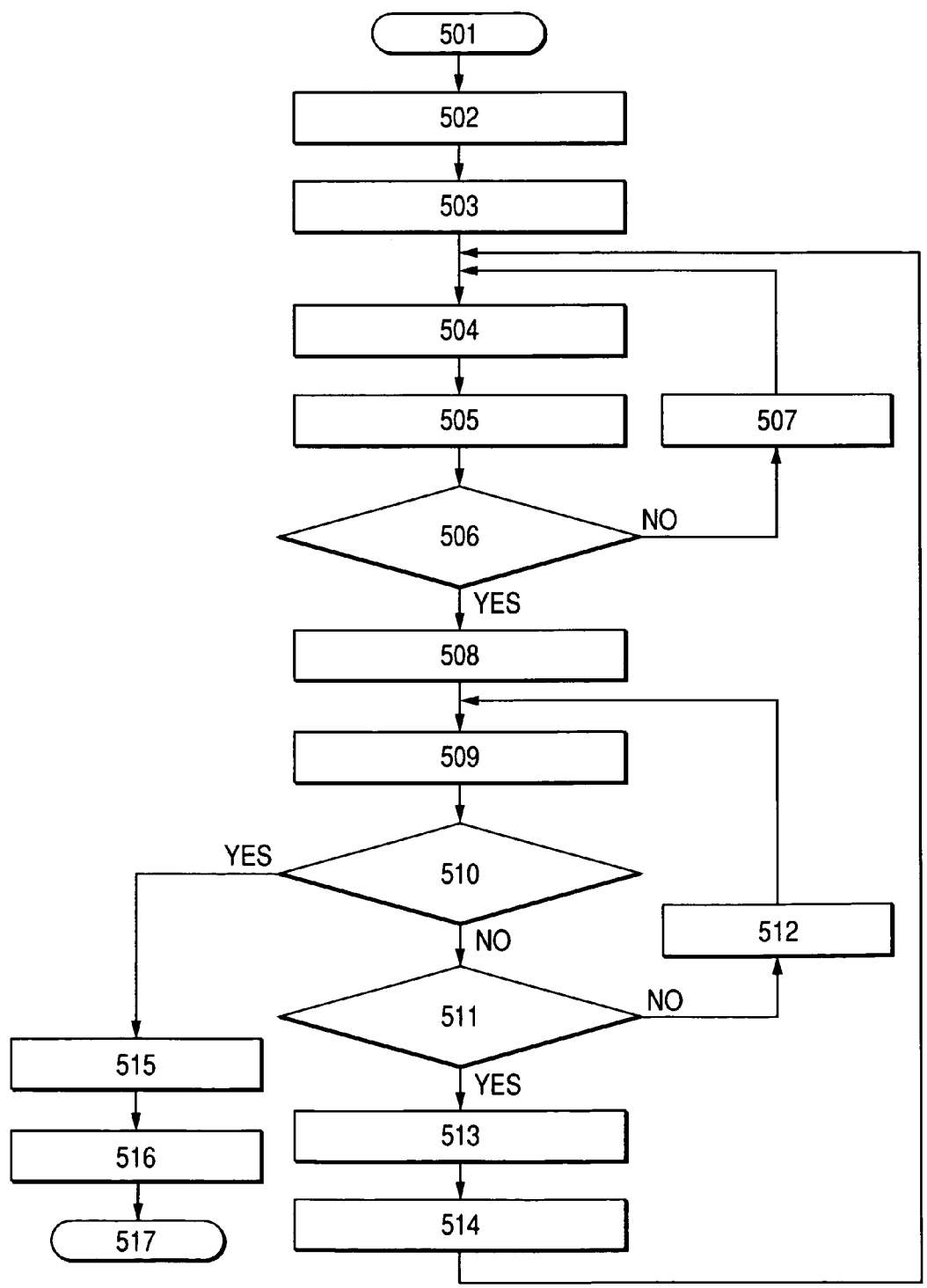
FIG. 9 is a flow chart showing an operation process for a sensor signal according to the embodiment 2 in the present invention.

An operation sequence when using a measuring apparatus comprising a sensor element according to the present embodiment will be now described with reference to FIG. 9.

A sequence from steps 401 to 407 in FIG. 6 and the sequence from steps 501 to 507 according to the present embodiment are the same.

When the apparatus has judged in the step 506 that data have been acquired from all working electrodes, the apparatus switches a channel to the first working electrode for detecting the crosstalk, in the step 508.

A current-detecting section detects a current in a working electrode for detecting a crosstalk in the step 509.

The apparatus judges whether the value of a detected current exceeds a predetermined limited value, in the step 510.

When the value of a current exceeds a limited value, the apparatus judges that a crosstalk occurs, immediately directs a current-detecting section to finish sampling and the apparatus to exit from a loop, statistically analyzes the current value sampled from each working electrode, in the step 515, and displays the concentration of each antigen obtained from the analysis result on a display, in the step 516. Then, the apparatus completes the operation, in the step 517.

When the value of a current does not exceed a predetermined limited value yet, the apparatus checks in the step 511 whether data have been acquired from all the working electrodes for detecting a crosstalk.

When data have not been acquired from all the working electrodes for detecting a crosstalk, the apparatus switches a measurement channel to a next working electrode for detecting the crosstalk in the step 512, and carries out the steps starting from the step 509 for measuring a current flowing through the working electrode for detecting the crosstalk.

When data have been acquired from all working electrodes for detecting a crosstalk, the apparatus waits a period of a sampling interval in the step 513, switches a measurement channel to a first working electrode in the step 514, and carries out the steps starting from the step 504 for measuring the value of a current flowing through each working electrode.

Embodiment 3

Figure 10:
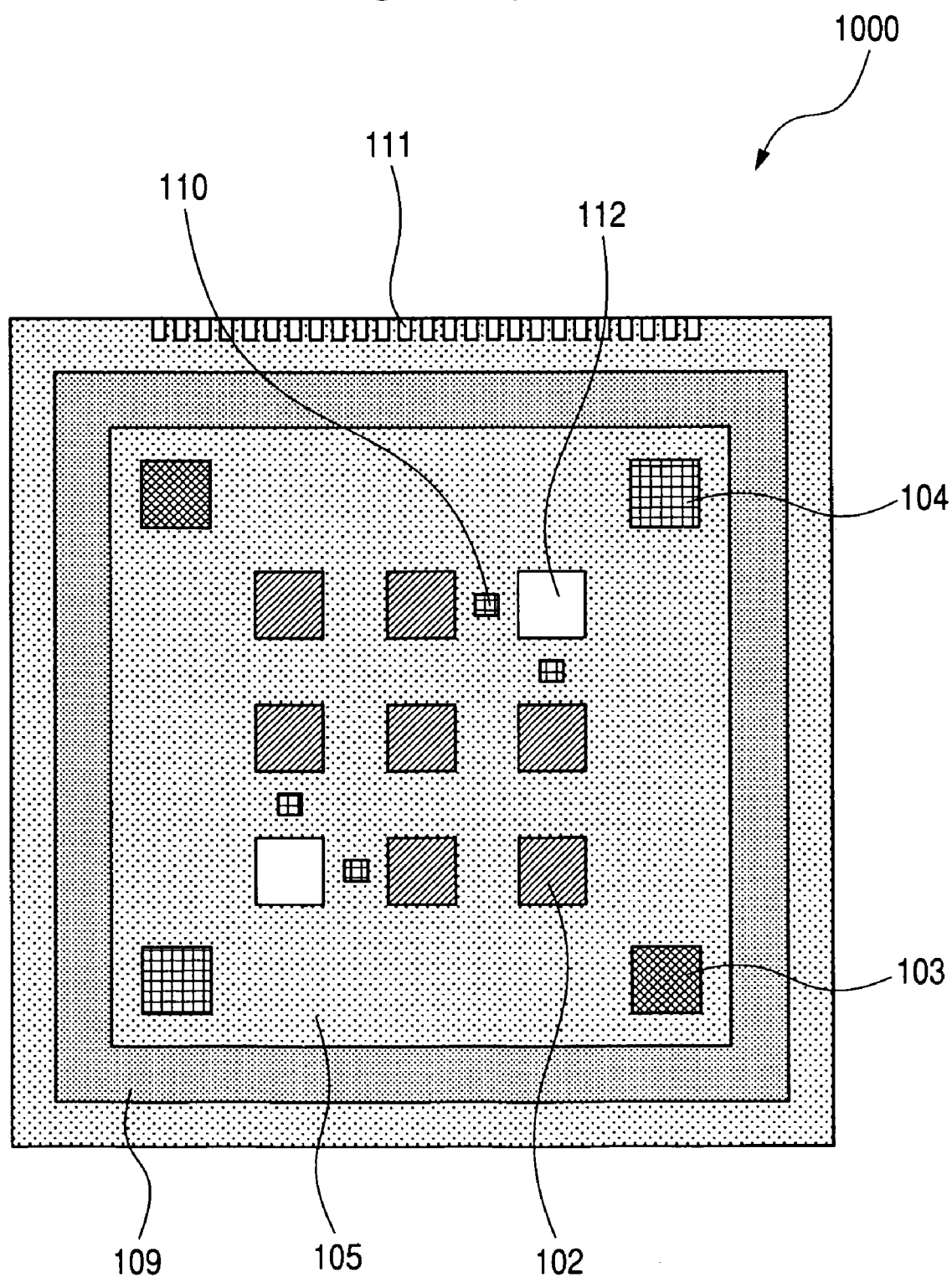
FIG. 10 is a plan view of a sensor element, showing a sensor according to the embodiment 3 in the present invention.

The configuration of a sensor element 1000 according to the embodiment 3 will be now described with reference to a plan view in FIG. 10. The sensor element 1000 is different from the sensor according to the embodiment 2 in the points of having further an enzyme-immobilized working electrode 112 and having a working electrode 110 for detecting a crosstalk only around the enzyme-immobilized working electrode 112. The enzyme-immobilized working electrode 112 is produced by the same method as that for producing the working electrode. An enzyme to be immobilized on the working electrode 112 is the same enzyme as the one which modifies a secondary antibody. The enzyme is immobilized by the same method as the method for immobilizing the antibody. An operation for the sensor element according to the present embodiment is completely the same as in the embodiment 2.

This application claims priority from Japanese Patent Application No. 2004-026813 filed Feb. 3, 2004, which is hereby incorporated by reference herein.

What is claimed is:

1. A sensor for detecting a target substance in a sample by detecting a product formed in the presence of an enzyme and an enzyme substrate comprising:
(A) two or more working electrodes;
(B) a first capturing molecule immobilized on the working electrodes to bind to the target substance;
(C) a current-detector for detecting a value of a current flowing through at least one of the working electrodes, when a composite comprising the first capturing molecule, the target substance, and a second capturing molecule modified with the enzyme has been formed on the working electrode, in order to detect the product formed when the enzyme substrate capable of acting with the enzyme is contacted with the enzyme;
(D) a target substance measuring apparatus having an arithmetic unit for determining an amount of the target substance in the sample based on the current value detected by the current-detector in a specified period of time after the enzyme has contacted with the enzyme substrate; and
(E) a crosstalk detecting electrode other than the working electrodes arranged between the working electrodes for detecting a crosstalk between the working electrodes, wherein the first capturing molecule is not immobilized on the crosstalk detecting electrode,
wherein the specified period of time is a time necessary for the current value through the crosstalk detecting electrode to exceed a particular value.

2. The sensor according to claim 1, wherein the target substance measuring apparatus determines a product amount from the current value, and determines the target substance amount in the sample from the product amount.

3. The sensor according to claim 1, wherein a different molecule is immobilized as a first capturing molecule on each of the working electrode.

* * * * *

UNITED STATES PATENT AND TRADEMARK OFFICE
CERTIFICATE OF CORRECTION

PATENT NO. : 7,195,738 B2  Page 1 of 1
APPLICATION NO. : 11/048749
DATED : March 27, 2007
INVENTOR(S) : Utsunomiya It is certified that error appears in the above-identified patent and that said Letters Patent is hereby corrected as shown below:

COLUMN 1:
Line 27, "other" should be deleted; and
Line 28, "than" should read -- other than --.

COLUMN 3:
Line 4, "catalyst-linkedlinked" should read -- catalyst -linked --.

COLUMN 6:
Line 28, "other" should be deleted; and
Line 29, "than" should read -- other than --.

COLUMN 9:
Line 40, "react" should read -- react with --;
Line 43, "react" should read -- react with --; and
Line 51, "maybe" should read -- may be --.

COLUMN 10:
Line 17, "the all" should read -- all the --;
Line 21, "the all" should read -- all the --; and
Line 22, "the all" should read -- all the --.

COLUMN 12:
Line 53 claim 3, "electrode." should read -- electrodes. --.

Signed and Sealed this

Eighteenth Day of March, 2008

JON W. DUDAS
*Director of the United States Patent and Trademark Office*